US009500608B2

(12) United States Patent
Mitchell et al.

(10) Patent No.: US 9,500,608 B2
(45) Date of Patent: Nov. 22, 2016

(54) EXAMINATION OF POROSITY BY NMR AND INTRUSION POROSIMETRY

(75) Inventors: Jonathan Mitchell, Great Cambourne (GB); Edmund Fordham, Cambridge (GB)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 511 days.

(21) Appl. No.: 14/005,254

(22) PCT Filed: Mar. 12, 2012

(86) PCT No.: PCT/IB2012/051152
§ 371 (c)(1),
(2), (4) Date: Sep. 13, 2013

(87) PCT Pub. No.: WO2012/123882
PCT Pub. Date: Sep. 20, 2012

(65) Prior Publication Data
US 2014/0002081 A1    Jan. 2, 2014

(30) Foreign Application Priority Data
Mar. 15, 2011   (GB) .................................. 1104325.4

(51) Int. Cl.
*G01V 3/00*       (2006.01)
*G01N 24/08*      (2006.01)
*G01N 15/08*      (2006.01)

(52) U.S. Cl.
CPC .......... *G01N 24/081* (2013.01); *G01N 15/088* (2013.01); *G01N 15/0886* (2013.01); *G01N 2015/0866* (2013.01)

(58) Field of Classification Search
CPC . G01N 24/81; G01N 15/088; G01N 15/0886

USPC ......................................................... 324/309
See application file for complete search history.

(56) References Cited

U.S. PATENT DOCUMENTS 4,644,779 A * 2/1987 Sisti ................... G01N 15/0886
                                                          73/38
6,362,624 B1   3/2002 Wand et al.
(Continued)

OTHER PUBLICATIONS

Cheng et al., Influence of pore size on the Knight shift in liquid tin and mercury in a confined geometry, J. Phys.: Condens. Matter 19, pp. 1-8, 2007.*
(Continued)

*Primary Examiner* — Daniel Miller

(57) ABSTRACT

Properties of a porous solid sample 19, which may be a core of rock taken from below ground are carried out using apparatus which performs both nuclear magnetic resonance (NMR) and porosimetry measurements. The apparatus has a magnet 11,12 providing a magnetic field and a radio frequency coil 20 for transmitting and/or receiving electromagnetic radiation so as to bring about NMR in the magnetic field, a pressure vessel 14, 15 to hold a sample 19 within the magnetic field, a supply of a non-wetting liquid connected to the vessel, means to apply pressure to the non-wetting liquid to force liquid into pores of the sample 19 means to measure applied pressure of the non-wetting liquid and means to measure volume thereof taken up by the sample. The pressure of non-wetting liquid may be increased in steps, using intruded liquid volume at each step to give a measurement of pore throat size using NMR at each step to give a measure of pore size such as diameter of equivalent sphere. The non-wetting liquid may be mercury and NMR may observe the Knight shift of 99 Hg.

16 Claims, 1 Drawing Sheet

(56) References Cited

U.S. PATENT DOCUMENTS

| | | |
|---|---|---|
| 7,352,179 B2 | 4/2008 | Chen et al. |
| 7,882,726 B2 | 2/2011 | Gupta et al. |
| 2006/0277011 A1 | 12/2006 | Tardy et al. |
| 2008/0100293 A1 | 5/2008 | Lucas et al. |
| 2011/0050223 A1* | 3/2011 | Balcom ................ G01R 33/305 324/307 |

OTHER PUBLICATIONS

"Micromeritics Porosimetry Brochure", ISO9001, Norcross, GA, 2001, 6 pages.

Baldwin, et al., "A direct method for simultaneously determining positive and negative capillary pressure curves in reservoir rock", Journal of Petroleum Science and Engineering, vol. 20, No. 3-4, Jun. 1998, pp. 161-165.

Bhattacharja, et al., "Microstructure determination of cement pastes by NMR and conventional techniques", Advanced Cement Based Materials, vol. 1, No. 2, Dec. 1993, pp. 67-76.

Borisov, et al., "Solidification and melting of mercury in a porous glass as studied by NMR and acoustic techniques", Physical Review B, vol. 58, 1998, pp. 5329-5335.

Brownstein, et al., "Importance of classical diffusion in NMR studies of water in biological cells", Phys. Rev. A., vol. 19, Jun. 1, 1979, pp. 2446-2453.

Carter, et al., "Metallic shifts in NMR", Chapter 2, The Knight Shift, Pergamon Press, 1977, 21 pages.

Charnaya, et al., "Influence of confined geometry on nuclear spin relaxation and self-diffusion in liquid indium", Physical Review B, vol. 70, 2004, p. 052201.

Charnaya, et al., "The Knight shift in liquid gallium confined within porous glasses and opals", Journal of Physics: Condensed Matter, vol. 15, No. 32, 2003, pp. 5469-5477.

Chen, et al., "What is the shape of pores in natural rocks?", Journal of Chemical Physics, vol. 116(19), May 2002, pp. 8247-8250.

Davies, et al., "Pore-Size Distributions from NMR Spin-Lattice Relaxation Data", Magnetic Resonance Imaging, vol. 9, 1991, pp. 681-685.

Davies, et al., "Pore-size distributions from nuclear magnetic resonance spin-lattice relaxation measurements of fluid-saturated porous solids. I. Theory and simulation", Journal of Applied Physics, vol. 67, 1990, pp. 3163-3170.

Davies, et al., "Pore-size distributions from nuclear magnetic resonance spin-lattice relaxation measurements of fluid-saturated porous solids. II. Applications to reservoir core samples", Journal of Applied Physics, vol. 67, 1990, pp. 3171-3176.

Frevel, et al., "Modifications in Mercury Porosimetry", Analytical Chemistry, vol. 35, No. 10, 1963, pp. 1492-1502.

Gane, et al., "Comparison of NMR Cryoporometry, Mercury Intrusion Porosimetry, and DSC Thermoporosimetry in Characterizing Pore Size Distributions of Compressed Finely Ground Calcium Carbonate Structures", Ind. Eng. Chem. Res., vol. 43, 2004, pp. 7920-7927.

Green, "Capillary Pressure Curves Determined by Direct Measurement of the Saturation using Magnetic Resonance Imaging", CWLS Magazine, vol. 28, No. 1, 2009, pp. 20-25.

Jehng, et al., "Pore structure of hydrating cement paste by magnetic resonance relaxation analysis and freezing", Magnetic Resonance Imaging, vol. 14, No. 7, 1996, pp. 785-791.

Jonas, "Nuclear Magnetic Resonance at High Pressures", Annu. Rev. Phys. Chem, vol. 26, 1975, pp. 167-190.

Kasperovich, et al., "NMR of mercury in porous carbon and silica gel", Physics of the Solid State, vol. 45 (9), Translated from Fizika Tverdogo Tela, Sep. 2003, pp. 1802-1807 and pp. 1717-1721.

Kumzerov, et al., "Freezing and melting of mercury in porous glass", Physical Review B, vol. 52, 1995, pp. 4772-4774.

Mitchell, et al., "Nuclear magnetic resonance cryoporometry", Physics Reports, vol. 461, No. 1, May, 2008, pp. 1-36.

Mitchell, et al., "Probing surface interactions by combining NMR cryoporometry and NMR relaxometry", Journal of Physics D: Applied Physics, vol. 38, No. 12, 2005, pp. 1950-1958.

Niessen, et al., "Recent Developments in Toroid Cavity Autoclave Engineering", Concepts in Magnetic Resonance Part B, vol. 16B (1), 2003, pp. 15-21.

Oleg, et al., "NMR cryoporometry: Principles, applications and potential", Progress in Nuclear Magnetic Resonance Spectroscopy, vol. 54, No. 2, Feb. 2009, pp. 97-122.

Petrov, et al., "NMR Cryoporometry: Principles, applications and potential", Progress in Nuclear Magnetic Resonance Spectroscopy, vol. 54, 2009, pp. 97-122.

Reverberi, et al., "Determination by experiment of the distribution function of the cylindrical macropores and ink bottles in porous systems", Annali di Chimica, vol. 56, 1966, pp. 1552-1561.

Rigby, et al., "Studies of the entrapment of non-wetting fluid within nanoporous media using a synergistic combination of MRI and micro-computed X-ray tomography", Chemical Engineering Science, vol. 16, 2006, pp. 7579-7592.

Ritter, "Pore-Size Distribution in Porous Materials", Industrial & Engineering Chemistry, vol. 17, No. 12, 1949, pp. 782-786.

Strange, et al., "Pressure Dependence of Translational Molecular Motion in Plastic Crystals", Mol. Cryst. Liq. Cryst., vol. 32, 1976, pp. 67-71.

Sun, et al., "Probing the internal field gradients of porous media", Physical Review E, vol. 65, 2002, pp. 051309-1-051309-7.

Tien, et al., "Influence of pore size on the Knight shift in liquid tin and mercury in a confined geometry", Journal of Physics: Condensed Matter, vol. 19, No. 10, 2007, p. 106217.

Washburn, "Note on a Method of Determining the Distribution of Pore Sizes in a Porous Material", Proceedings of the National Academy of Sciences, vol. 7, No. 4, 1921, pp. 115-116.

Zimmerman, et al., "Nuclear Magnetic Resonance Studies in Multiple Phase Systems: Lifetime of a Water Molecule in an Adsorbing Phase on Silica Gel", J. Phys. Chem., vol. 61, Oct. 1957, pp. 1328-1333.

* cited by examiner

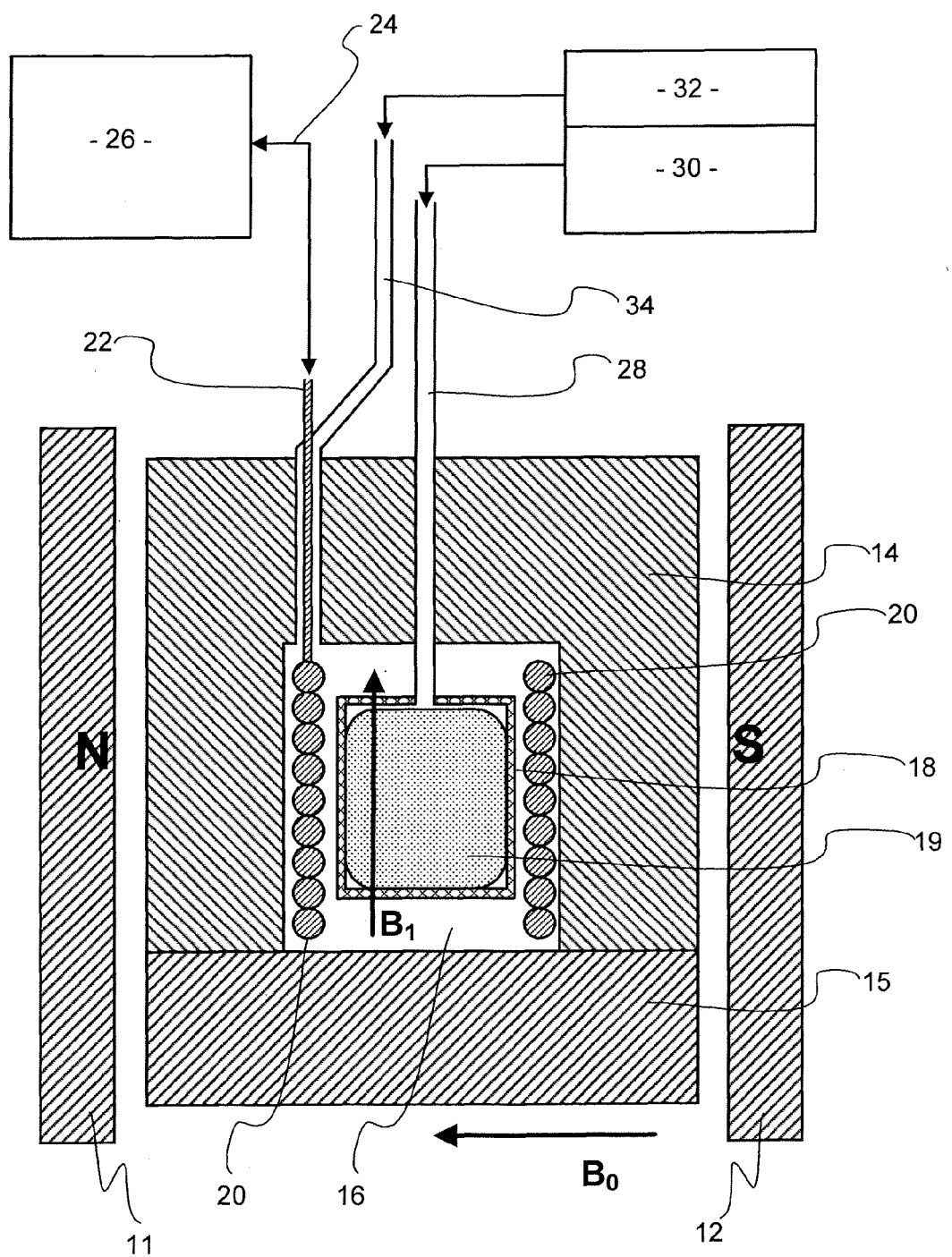

EXAMINATION OF POROSITY BY NMR AND INTRUSION POROSIMETRY

CROSS-REFERENCE TO RELATED APPLICATIONS

This application is a United States National Stage Application under 35 U.S.C. §371 and claims priority to Patent Cooperation Treaty Application Number PCT/IB2012/051152 filed Mar. 12, 2012, which claims priority to British Patent Application No. GB1104325.4 filed Mar. 15, 2011. Both of these applications are incorporated herein by reference in their entireties.

FIELD OF THE INVENTION

This invention is concerned with the determination of properties of pores in porous solids and thus concerns testing of materials. The invention is not limited to specific reasons for testing nor to samples of specific origin, but it may be applied to porous rock cores collected as samples underground whilst drilling. The collection of such samples and their examination may be done in connection with exploration for, or exploitation of, hydrocarbons in underground reservoirs. It is also possible that it may be done in connection with exploration for, or utilisation or management of underground water, or in connection with schemes for the storage of captured carbon dioxide.

BACKGROUND OF THE INVENTION

There are many circumstances where it is desired to make measurements of the properties of pores in a porous material. One such is the testing of samples of porous rock.

It is conventional practice when drilling through underground rock to drill around a central cylinder of rock which is subsequently detached and brought to the surface as a sample, habitually referred to as a rock core. Rock cores may be subjected to various testing procedures at the surface, including tests to determine sizes of pores. For most natural porous media the pores have a somewhat complex geometry. Suggested representations of the geometry have included a ball-and-stick model and a series of intersecting spheres. Information on the size of pores present in oil-bearing rock is important for the understanding of fluid transport and hence oil recovery.

Mercury intrusion porosimetry (MIP) is a standard analytical method for measuring a distribution of pore sizes in a porous material. Mercury is routinely used for this test because it does not wet the surface of the sample. Liquid mercury is forced into a small sample of rock under elevated pressure which opposes capillary pressure resulting from ingress of non-wetting liquid into pores. The total porosity of the sample is determined as the total volume of mercury injected. A measurement related to pore size can also be made because the pressure required to force the non-wetting liquid mercury into an empty pore rises as the pore access size (the size of the confining space through which the mercury must pass to fill the void) diminishes. For most natural porous media this access size does not represent overall pore size but generally corresponds to the pore throat diameter. A size distribution is normally determined by increasing the pressure in steps and observing the cumulative volume intruded at each step. This procedure can produce a graph or histogram of pore volumes plotted against size.

MIP is normally carried out using a sample which has previously been placed under vacuum, so that the mercury is intruded into empty pores. However, it can also be used in other experimental procedures, for instance to determine the capillary pressures present in a sample as a non-wetting liquid displaces air. Intrusion porosimetry has also been carried out with other liquids as alternatives to mercury, sometimes seeking to use a liquid which does not have toxicity issues associated with it. However, mercury continues to be the preferred non-wetting liquid for much intrusion porosimetry.

A more recent method for determining pore size distributions is by measurements of nuclear magnetic resonance (NMR). Several NMR methods have been used. For example Davies et al in J. Appl. Phys. vol 67 pages 3163-3170 and pages 3171-3176 (1990) related the spin-lattice relaxation time $T_1$ to distribution of pore size which was taken as size of an equivalent sphere. Mitchell et al in J. Phys.D: Appl. Phys. vol 38 pages 1950-58 (2005) state that the spin-spin relaxation time $T_2$ of a liquid saturating a porous medium will be inversely proportional to the surface-to-volume ratio of the pores. However, this use of relaxation time is hindered by a lack of knowledge regarding the relaxivity, which affects the scale of the results. Relaxivity is dependent on properties of the rock sample including the density of paramagnetic species in the rock matrix (present, in particular, in clays) and the diffusion of the liquid molecules to and on the solid surface. Relaxivity has been seen to vary considerably even between chemically similar materials.

SUMMARY OF THE INVENTION

Broadly this invention provides the application of both liquid intrusion and NMR spectroscopy to a porous sample. In forms of this invention this will entail accommodating a pressure vessel for the sample within the magnetic field of the NMR magnet.

In one aspect, this invention provides a method of determining properties of a porous solid sample, comprising driving a non-wetting liquid under pressure into pores of the sample and carrying out nuclear magnetic resonance (NMR) measurements on liquid which has entered pores of the sample. The non-wetting liquid may be mercury, in which case the NMR measurements are carried out on a natural isotope of mercury (which is in contrast to the known application of proton NMR to determination of pore properties).

The $^{199}$Hg isotope has a stable, spin-½ nucleus with 16.87% natural abundance, and a gyromagnetic ratio of $7.59\times10^6$ Hz T$^{-1}$. As a consequence, a measurement of $^{199}$Hg is many times less sensitive than a measurement of $^1$H (the most common nucleus probed with NMR). Nevertheless, $^{199}$Hg NMR can be carried out successfully and has been reported in various literature articles.

Some forms of this invention include making a direct measurement of the volume of liquid entering the sample as in conventional intrusion porosimetry. However, it is within the scope of this invention to use applied pressure to force liquid into pores of a sample but rely solely on NMR for measurements.

In some forms of this invention the liquid is driven into the sample by pressure which is progressively increased, with measurements of volume and/or NMR measurements being carried out repeatedly as the pressure is increased. The pressure may be increased in steps, with measurement of volume and/or NMR measurement at each pressure step.

(This adapts the known MIP procedure of increasing the pressure of the mercury in steps and measuring the volume of mercury forced into the sample at each pressure step). It may be convenient to make a measurement of volume and an NMR measurement at each pressure step, or possibly to make only one of these measurements at some pressure steps.

As already mentioned, the non-wetting liquid may be mercury, which is of course an electrically conducting liquid. Electrical conductivity of a liquid limits the extent to which a radio-frequency field can penetrate into the material to cause the excitation which is fundamental to NMR. Consequently conductivity limits excitation to a surface layer having a depth (referred to as a skin-depth) which is dependent on the frequency which in turn is dependent on the strength of the magnetic field. The skin depth may be in the region of 100 micron, which would block the application of NMR to a conductive liquid in bulk. Nevertheless, it is possible to carry out NMR when the liquid is present in small particles, as is often the case when liquid has entered the pores of rock, because these often have a pore diameter below 100 micron.

The conductive electrons in an electrically conducting material cause the NMR spectral line to undergo a frequency shift, termed the Knight shift. The Knight shift is normally observed by Fourier transform of the time domain NMR signal and is a shift relative to the resonance frequency of a bulk sample of the liquid. It has been observed that when conducting liquid is confined in small pores and so forced to have a small particle size, the magnitude of the Knight shift is inversely dependent on the particle size enforced by the surrounding porous structure.

Observation of this phenomenon has been reported for gallium by Chernaya et al in J. Phys: Condens. Mater. vol 15 pages 5469-5477 (2003) and subsequently for mercury and tin by Tien et al in J. Phys: Condens. Mater. vol 19 106217 (2007).

Unlike other NMR methods for determining pore body size, such as proton NMR relaxometry, the Knight shift is dependent only on pore body size and is not related to other properties of the sample. Hence the pore body size can be determined independently of other properties such as pore throat size. A possible alternative to measurement using the Knight shift would be $^{199}$Hg NMR relaxometry: obtaining a pore body size from $T_1$ or $T_2$ relaxation measurement of $^{199}$Hg.

It can thus be appreciated that information obtainable by NMR is different from information obtainable by intrusion porosimetry. If the two techniques are used together, the information obtained can be combined, as follows. The applied pressure is increased in steps. At each step the cumulative volume of liquid which has entered the pores is measured and an NMR measurement of pore body size is also made. The total volume of liquid which has entered the sample at the highest porosity is taken as the total pore volume of the sample.

The porosimetry measurement of volume at each pressure step records both the applied pressure and the volume which has entered at that pressure. In accordance with conventional porosimetry, the pore throat size can be calculated from the applied pressure at each pressure step and the increment in volume which has entered the pores since the previous pressure is the fraction of total pore volume having that pore throat size. The NMR measurement at each pressure step gives the pore body size encountered by the liquid which has entered the pores, and so the change in pore body size since the previous measurement provides a value or range of pore body size associated with the pore throat size. Thus a pore body-to-throat ratio can then be determined as a function of liquid injection pressure. These simultaneous measurements of pore throat and pore body size can be used as inputs to computational methods for predicting connectivity of the pore structure and flow conductivity through the porous rock. An illustration of a computational approach to predicting flow conductivity is provided by US published patent application 2006/0277011.

It may be noted that the fraction of total pore volume filled at each pressure step can be determined in two ways. As mentioned in the previous paragraph, it is the increment in liquid volume which has entered since the previous pressure step, as a fraction of total liquid volume. It is also the increment in NMR signal intensity at each pressure step, as a fraction of the total NMR signal intensity at the highest pressure.

A schematic illustration of apparatus for the present invention will now be described by way of example, with reference to the drawing. This description is exemplary in nature and is not intended to limit the scope of the invention.

BRIEF DESCRIPTION OF THE DRAWING

The drawing is a schematic cross sectional view of combined porosimetry and NMR apparatus.

DETAILED DESCRIPTION

The apparatus shown in the drawing has a pair of permanent magnets 11, 12 arranged on a common axis facing each other but spaced apart so that there is a static magnetic field between them as indicated by the arrow $B_0$. The magnetic field $B_0$ extends from a S pole piece provided by magnet 12 to a N pole piece provided by magnet 11. In this illustration the magnets 11, 12 are positioned so that the static magnetic field $B_0$ is horizontal. However, the apparatus could be placed at some other orientation if convenient. Both permanent magnets 11, 12 may be made of rare earth compounds to give a high magnetic field. Specifically, they may possibly be neodymium iron boron (NdFeB) magnets which can be manufactured in the required shapes or assembled from smaller blocks. The permanent magnets 11, 12 should desirably provide a magnetic field $B_0$ which is uniform within the space between the magnets.

A pressure vessel, which is formed in two parts 14, 15 secured together so as to allow access to an interior chamber 16, is positioned within the magnetic field. The pressure vessel 14, 15 is made of a non-magnetic material with high tensile strength, such as brass so that it provides pressure containment without eliminating the $B_0$ magnetic field. Inside this pressure vessel, the chamber 16 contains an inner sample enclosure 18 inside which is a sample 19 under test. The chamber 16 also contains a radio-frequency coil 20 surrounding the sample. This coil has a vertical axis and so induces a magnetic field in the vertical direction, denoted by arrow $B_1$ which is of course orthogonal to the static field $B_0$.

A connection to the radio-frequency coil 20 is provided at 22 and this is connected by coaxial cable 24 to the electronic systems of an NMR spectrometer 26 for providing radio frequency signals to the coil 20 and receiving radio frequency signals from it.

Because the radio frequency emission from the coil 20 cannot penetrate a conductive material such as brass, the radio frequency coil 20 is located inside the brass pressure vessel 14, 15. This necessitates providing a pressure tolerant connection 22 to the coil 20. A possible alternative arrangement would use a polymer composite material for the pressure vessel. Such a material can be both non-magnetic and transparent to radio-frequency radiation, so allowing the radio-frequency coil 20 to be located outside the pressure vessel 14, 15.

A mercury capillary 28 leads to the sample chamber from standard MIP apparatus 30 which is able to supply mercury at a range of controlled pressures along the capillary and measure the volume of mercury delivered into the sample 19.

A pressure pump 32 is connected by conduit 34 to the chamber 16 and pressurizes the chamber 16, outside the sample enclosure 18 with a gas or liquid which is transparent to the magnetic fields and the radio frequency signals from coil 20. This pressure pump 32 is controlled to co-ordinate with the pressure applied to mercury by the MIP apparatus 30 and maintains a pressure outside the sample enclosure 18 which is equal to, or slightly above, the mercury pressure applied to the sample 19 in the enclosure 18.

To examine a sample 19 using this apparatus, the sample is drained of any liquid, under vacuum if necessary, and placed in the sample enclosure 18. The capillary 28 and sample enclosure 18 are placed under vacuum by means of a pump in the MIP apparatus. Mercury is then admitted to the sample enclosure 18 without any application of positive pressure. This creates the starting point for an experimental run.

A base line NMR measurement is made, measuring energy absorbed, or emitted at frequencies in a range covering the $^{199}$Hg resonance frequency modified by the Knight shift. Next the pressure of mercury applied to the sample 19 is increased in a series of steps. After reaching equilibrium at each pressure step the cumulative volume of mercury forced into the sample 19 is measured by the MIP apparatus and an NMR measurement is made, to observe the changes in NMR spectrum and overall NMR signal strength as mercury is forced into the sample 19 under pressure.

The invention claimed is:

1. A method of determining properties of a porous solid sample, comprising
   driving a non-wetting liquid under a plurality of applied pressures into pores of the sample and
   carrying out one or more nuclear magnetic resonance (NMR) measurements on liquid which has entered pores of the sample at each applied pressure.

2. A method according to claim 1 wherein the non-wetting liquid is mercury.

3. A method according to claim 1 which also comprises measuring a volume of the non-wetting liquid which has entered the sample.

4. A method according to claim 1 which comprises driving the non-wetting liquid into the sample under a plurality of applied pressures and measuring the volume of the non-wetting liquid which has entered the sample under each applied pressure.

5. A method according to claim 1 wherein the non-wetting liquid is conductive and the NMR measurements are measurements of the Knight shift of the resonant frequency of nuclei of the conductive non-wetting liquid.

6. A method according to claim 1 wherein the NMR measurements are measurements of $T_1$ or $T_2$ relaxation time of the non-wetting liquid.

7. A method according to claim 1 wherein the porous sample is a rock core.

8. A method according to claim 2, wherein the NMR measurements are measurements of the Knight shift of the resonant frequency of nuclei of the mercury.

9. Apparatus for determining properties of a porous solid sample, comprising
   a nuclear magnetic resonance (NMR) spectrometer including a magnet providing a magnetic field and a radiofrequency coil for transmitting and/or receiving electromagnetic radiation, the coil having a coil axis extending transverse to the magnetic field,
   a pressure vessel to hold a sample within the magnetic field, a supply of a non-wetting liquid connected to the vessel, means to apply a plurality of applied pressures to the non-wetting liquid to force liquid into pores of the sample,
   means to measure applied pressure of the non-wetting liquid and volume thereof taken up by the sample;
   wherein the pressure vessel is formed of a non-magnetic material and is located within the magnetic field, and the spectrometer is configured to make NMR measurements on the non-wetting liquid in pores of the sample at each applied pressure.

10. Apparatus according to claim 9 wherein the means to apply pressure is configured to increase the applied pressure in incremental steps.

11. Apparatus according to claim 9 wherein the non-wetting liquid is conductive and the spectrometer is configured to measure Knight shift of the magnetic resonance frequency of nuclei of the non-wetting liquid in pores of the sample.

12. Apparatus according to claim 9 wherein the spectrometer is configured to measure $T_1$ or $T_2$ relaxation time of the non-wetting liquid in pores of the sample.

13. Apparatus according to claim 9 wherein the non-wetting liquid is mercury.

14. Apparatus according to claim 9 wherein the radiofrequency coil is located within the pressure vessel.

15. Apparatus according to claim 9, wherein the non-wetting liquid is mercury and the spectrometer is configured to measure Knight shift of the magnetic resonance frequency of nuclei of the mercury in pores of the sample.

16. A method of determining properties of a porous solid sample, comprising
   driving a non-wetting liquid under pressure into pores of the sample and
   carrying out one or more nuclear magnetic resonance (NMR) measurements on liquid which has entered pores of the sample;
   wherein the non-wetting liquid is mercury and the method comprises driving the mercury into the sample under a plurality of applied pressures, measuring the volume of mercury which has entered the sample under each applied pressure and making an NMR measurement on the mercury which has entered the sample at each applied pressure.

* * * * *